(12) United States Patent
Ravikumar et al.

(10) Patent No.: US 8,230,863 B2
(45) Date of Patent: Jul. 31, 2012

(54) PLATFORM FOR FIXING SURGICAL INSTRUMENTS DURING SURGERY

(75) Inventors: Sundaram Ravikumar, Briarcliff Manor, NY (US); H. Allan Alward, Shelton, CT (US); Steven J. Wysocki, Stratford, CT (US); Guy L. Osborne, Trumbull, CT (US)

(73) Assignee: Mini-Lap Technologies, Inc., Dobbs Ferry, NY (US)

( * ) Notice: Subject to any disclaimer, the term of this patent is extended or adjusted under 35 U.S.C. 154(b) by 1094 days.

(21) Appl. No.: 11/668,169

(22) Filed: Jan. 29, 2007

(65) Prior Publication Data

US 2007/0277815 A1    Dec. 6, 2007

Related U.S. Application Data

(63) Continuation-in-part of application No. 11/420,927, filed on May 30, 2006, now Pat. No. 7,766,937.

(60) Provisional application No. 60/828,916, filed on Oct. 10, 2006.

(51) Int. Cl.
| | | |
|---|---|---|
| A61G 5/00 | (2006.01) |
| A61G 7/053 | (2006.01) |
| A47B 71/00 | (2006.01) |
| A47B 7/00 | (2006.01) |
| A47C 20/00 | (2006.01) |
| A61B 19/00 | (2006.01) |
| A61B 6/04 | (2006.01) |
| A61B 1/32 | (2006.01) |
| A61F 5/37 | (2006.01) |
| A45D 19/04 | (2006.01) |
| A47J 47/16 | (2006.01) |
| F16M 11/00 | (2006.01) |
| F16M 11/02 | (2006.01) |
| H05G 1/00 | (2006.01) |
| F16B 7/10 | (2006.01) |
| F16B 7/06 | (2006.01) |
| F16C 11/00 | (2006.01) |
| F16C 11/06 | (2006.01) |
| F16D 1/12 | (2006.01) |
| F16D 3/00 | (2006.01) |

(52) U.S. Cl. ........ 128/845; 128/869; 128/870; 248/127; 248/160; 248/176.1; 248/177.1; 248/178.1; 378/208; 378/209; 5/81.1 R; 5/600; 5/621; 5/630; 403/53; 403/55; 403/56; 403/57; 403/58; 403/59; 600/201; 600/228; 600/229

(58) Field of Classification Search ................ 128/99.1, 128/845; 403/53, 55–58; 600/228, 229; 248/160, 181.1, 181.2, 288.31, 481; 5/601; 378/205, 208, 209
See application file for complete search history.

(56) References Cited

U.S. PATENT DOCUMENTS

| | | |
|---|---|---|
| 2,890,801 A | 6/1959 | Ladd et al. |
| 4,193,198 A | 3/1980 | Bauer |
| 4,573,452 A | 3/1986 | Greenberg |
| D293,470 S | 12/1987 | Adler |
| 4,867,404 A | 9/1989 | Harrington et al. |
| 4,949,927 A | 8/1990 | Madocks et al. |

(Continued)

*Primary Examiner* — Patricia Bianco
*Assistant Examiner* — Brandon L Jackson
(74) *Attorney, Agent, or Firm* — Gordon & Jacobson, PC

(57) ABSTRACT

A medical assembly includes a platform which is securely mountable to an operating room fixture, and a plurality of arms or arm modules coupled to the platform and each with a grasper for holding a surgical instrument or port. The medical assembly is particularly applicable for laparoscopic surgery although it is not limited thereto.

22 Claims, 9 Drawing Sheets

U.S. PATENT DOCUMENTS

| | | |
|---|---|---|
| 5,284,130 A | 2/1994 | Ratcliff |
| D388,515 S | 12/1997 | Bookwalter et al. |
| D389,242 S | 1/1998 | Bookwalter et al. |
| D389,913 S | 1/1998 | Bookwalter et al. |
| 5,775,334 A * | 7/1998 | Lamb et al. .................. 128/845 |
| 5,865,780 A * | 2/1999 | Tuite ............................... 602/32 |
| 5,899,425 A | 5/1999 | Corey, Jr. et al. |
| 6,155,439 A | 12/2000 | Draughn |
| 6,248,062 B1 | 6/2001 | Adler et al. |

* cited by examiner

PLATFORM FOR FIXING SURGICAL INSTRUMENTS DURING SURGERY

PRIORITY

This application claims the benefit of provisional application Ser. No. 60/828,916 filed Oct. 10, 2006 and is a continuation-in-part of U.S. Ser. No. 11/420,927 filed May 30, 2006 now U.S. Pat. No. 7,766,937, both of which are incorporated herein in their entireties.

BACKGROUND OF THE INVENTION

1. Field of the Invention

This invention relates broadly to devices which assist physicians in the use of medical instruments during surgery. More particularly, this invention relates to a platform that can be used to maintain medical instruments in a fixed position during surgery. The invention has particular application to laparoscopic-type surgery, although it is not limited thereto.

2. State of the Art

Over the last two decades, minimally invasive surgery has become the standard for many types of surgeries which were previously accomplished through open surgery. Minimally invasive surgery generally involves introducing an optical element (e.g., laparoscope or endoscope) through a surgical or natural port in the body, advancing one or more surgical instruments through additional ports or through the endoscope, conducting the surgery with the surgical instruments, and withdrawing the instruments and scope from the body. In laparoscopic surgery (broadly defined herein to be any surgery where a port is made via a surgical incision, including but not limited to abdominal laparoscopy, arthroscopy, spinal laparoscopy, etc.), a port for a scope is typically made using a surgical trocar assembly. The trocar assembly often includes a port, a sharp pointed element (trocar) extending through and beyond the distal end of the port, and at least in the case of abdominal laparoscopy, a valve on the proximal portion of the port. Typically, a small incision is made in the skin at a desired location in the patient. The trocar assembly, with the trocar extending out of the port is then forced through the incision, thereby widening the incision and permitting the port to extend through the incision, past any facie, and into the body (cavity). The trocar is then withdrawn, leaving the port in place. In certain circumstances, an insufflation element may be attached to the trocar port in order to insufflate the surgical site. An optical element may then be introduced through the trocar port. Additional ports are then typically made so that additional laparoscopic instruments may be introduced into the body.

Trocar assemblies are manufactured in different sizes. Typical trocar port sizes include 5 mm, 10 mm and 12 mm (available from companies such as Taut and U.S. Surgical), which are sized to permit variously sized laparoscopic instruments to be introduced therethrough including, e.g., graspers, dissectors, staplers, scissors, suction/irrigators, clamps, forceps, biopsy forceps, etc. While 5 mm trocar ports are relatively small, in some circumstances where internal working space is limited (e.g., children), it is difficult to place multiple 5 mm ports in the limited area. In addition, 5 mm trocar ports tend to limit movements of instruments inside the abdominal cavity.

Further, while laparoscopic surgery has reduced the trauma associated with various surgical procedures and has concomitantly reduced recovery time from these surgeries, there always remains a desire in the art to further reduce the trauma to the patient.

One area of trauma associated with laparoscopic surgery identified by the inventor hereof as being susceptible of reduction are the scars which result from the trocar ports used. In many laparoscopic surgeries, three or more trocar incisions are made. For example, in laparoscopic hernia repair surgery, four trocar incisions are typically made, with one incision for insufflating the abdomen and inserting the optical device, two incisions for trocar ports for inserting graspers therethrough, and a fourth port for passing a stapler therethrough. Those skilled in the art and those who have undergone surgical procedures recognize that even the 5 mm trocar ports leave holes which must be stitched and which result in scars.

A second area of trauma associated with laparoscopic surgery identified by the inventor hereof as being susceptible of reduction relates to trauma resulting from the manipulation (angling) of the trocar ports required in order to conduct the surgery due to inexact placement. Angling of the port can cause tearing at the incision periphery.

In order to overcome the trauma associated with laparoscopic surgery, the parent application Ser. No. 11/420,927 discloses a minimally invasive surgical assembly including a 2 mm needle and a retractor extending through the needle. The needle retractor of the parent application has the potential of eliminating or reducing the need for using larger trocar ports in certain surgeries. Where the surgery calls for retracting organs, multiple needle retractors can be required. As with other endoscopic and laparoscopic instruments available on the market, the needle retractor of the parent application includes a shaft which may be attached to an operating room table via a holder which holds the assembly in place. To hold multiple instruments in place, multiple holders are needed.

Those skilled in the art will appreciate that because of the number of laparoscopic tools used in a laparoscopic surgery, the maintenance of these tools at fixed locations within a patient during surgery can be difficult. Thus, there remains a need in the art to provide a convenient means for securing these instruments in a fixed location relative to the patient during surgery.

SUMMARY OF THE INVENTION

It is therefore an object of the invention to provide a platform for assisting minimally invasive surgery which remains in a fixed position relative to a patient being operated on and which is capable of holding two or more surgical instruments.

It is another object of the invention to provide a platform having a plurality of arms for holding surgical instruments in a fixed position relative to a patient.

It is a further object of the invention to provide a medical assembly for holding a plurality of surgical instruments during minimally invasive surgical procedures such as endoscopic and laparoscopic surgery.

In accord with these objects, which will be discussed in detail below, a medical assembly according to the invention broadly includes a platform and a plurality of arms or arm modules coupled to the platform each with a grasper for holding a surgical instrument. The medical assembly is particularly applicable for laparoscopic surgery although it is not limited thereto.

The platform of the present invention preferably includes structure for affixing the platform in position relative to a patient on an operating room table, and structure for receiving the arms of the assembly. The structure for affixing the platform in position can be, for example, a hole in the platform which receives a structural support pole and a knob or other mechanism for engaging the pole. In this manner, the platform positioning can be adjusted in a desired manner. The pole in turn is attached to a fixture (e.g. an operating table or bed) in an operating room. With the platform affixed to the pole, the location of the platform relative to the patient is fixed. In one embodiment, the platform structures for receiving the arms include rails or grooves onto which or into which the arm modules can slide. In another embodiment, the platform structure for receiving the arms of the assembly is integral with the portion of the platform which receives the support pole and includes two or more receptacles which receive the arms or arm modules.

In a preferred embodiment, the arms are modules having proximal ends which are coupled to the platform, flexible middle portions, and distal ends onto which the graspers are fixed. The arms preferably include a plurality of arm segments coupled by ball and socket joints through which a tightening element such as a cable extends. The joints allow the surgeon to directionally adjust the shape and position of each arm into a desired configuration. The cable terminates on the platform end at a winch-type mechanism which can be used to fix (tighten) the arm in its desired configuration. On its distal end, the cable terminates by being captured by the grasper.

The graspers are positioned at distal ends of respective arms. The graspers are used to hold surgical instruments. Most preferably, each grasper has a proximal connector to its associated arm, as well as handles, and distal grasping elements. The proximal connector is adapted to receive the end arm element and the cable and hold the cable in tension. The arms are coupled to the proximal connector and to the distal grasping elements. When squeezed together, the handles cause the grasping elements to open, and when released, the handles return to an at-rest position where the grasping elements close. The grasping elements may take any of various forms but are preferably jaw-type elements which can grasp and securely hold a shaft of a laparoscopic instrument. Different graspers may be provided to receive different surgical instruments; e.g., instruments of different shaft diameters.

It will be appreciated by those skilled in the art that multiple surgical instruments are likely to be used at the same time in conducting surgical procedures. The use of multiple surgical instruments is particularly common in laparoscopic surgical procedures. Indeed, it is likely that multiple cutting, clamping, and retracting instruments may be used together to simultaneously hold organs out of harms way while making an incision into a targeted organ or tissue structure. The assembly of the present invention is useful in holding those instruments in place relative to the patient while the surgeon is manipulating one of the instruments.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
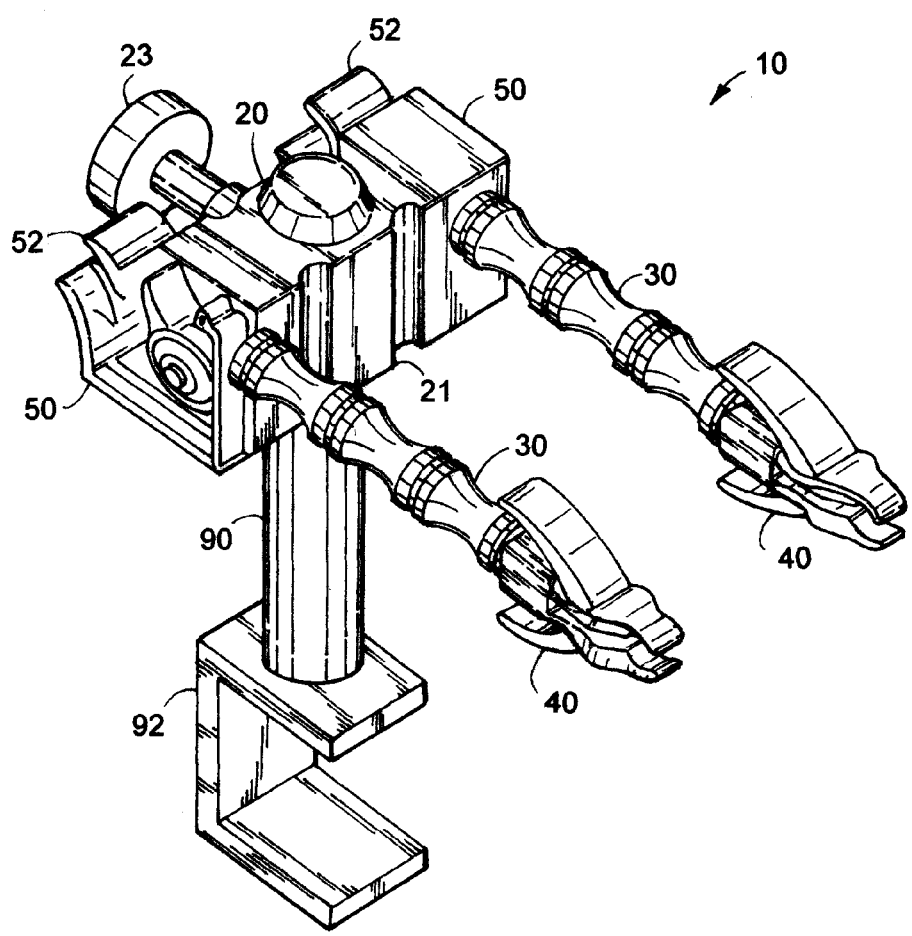
FIG. 1 is a partially transparent perspective view of a medical assembly coupled to a medical pole according to a first embodiment.

The present invention is directed to a medical assembly having a platform and a plurality of arms coupled to the platform each with a grasper at its distal end for holding a surgical instrument in a fixed position relative to a patient.

Turning now to FIGS. 1-8, a medical assembly 10 is shown in a first embodiment having a platform 20, a plurality of arms 30 (two shown) extending distally from the platform 20, and graspers 40 located on the distal ends of the arms 30. The platform 20 preferably includes structure for affixing the platform in position relative to a patient on an operating room table, and structure for receiving the arms of the assembly. In a preferred embodiment, the platform 20 preferably includes a central portion 21 which acts as a nexus upon which other elements of the medical assembly 10 may be adjoined. Central portion 21 defines a first hole 22a and a second threaded hole 22b. The first hole 22a is designed to receive a support pole 90 which in turn is coupled to a bracket 92 or other mechanism such as a clamp, clasp, bolt, etc. for affixing the pole 60 to a fixture (e.g. an operating table or bed—not shown) in an operating room. Alternatively, an operating table or fixture can be modified such that the pole 90 is inserted directly through a portion of the fixture to provide the needed stability and support for the central portion 21 of the platform 20. The second hole 22b is designed to receive a threaded knob 23 or other mechanism for engaging the pole. More particularly, the hole 22a is optimally sized so that when the pole 90 is inserted through the hole 22a, the platform 20 is slidably fixed along a longitudinal axis defined by the length of the pole 90. The knob 23 is then used to extend through hole 22b and fix the platform 20 relative to the pole 90. When the knob 23 is engaged, the platform 20 is fixed such that the platform cannot move in either the longitudinal direction along the length of the pole 90 or in a rotational manner around the pole 90. In this manner, the platform positioning can be adjusted in a desired manner with the location of the platform relative to the patient being fixed.

As an alternative example and not by way of limitation, the platform 20 may include protrusions and the pole 90 may include grooves along its longitudinal axis such that when the pole 90 is inserted into the hole 22, the protrusions engage the grooves to prevent rotational motion of the platform 20 about the pole 90. Similarly, any number of male-female combinations may be used to engage the pole 90 thus preventing motion along the direction defined by the longitudinal axis of the pole 90. An example of such a male-female combination includes peg and notch or hole elements wherein the pole 90 contains a series of notches or holes for engagement by a peg contained on the platform 20. In another embodiment, the platform 20 itself may simply be affixed to a fixed structure in the operating room without the use of the pole 90.

As previously mentioned, the platform 20 also includes structure for receiving the arms 30 of the assembly. In a first embodiment discussed hereinafter with respect to FIGS. 7 and 8, the platform structure for receiving the arms 30 comprises a rail and groove structure such that a housing or mount 50 on the proximal portion of the arms can slide into engagement with the platform. By providing platform 20 with one rail and one groove, and the housing of the proximal portion of the arms with one rail and one groove, a modular system is generated so that as many arms as necessary can be added to the system. In a second embodiment, the arm receiving structure comprises arm mount receptacles which are integral with the central portion 21. The receptacles include top doors or slots in their top walls in order to receive the proximal portions of the arms, and a slot in the front wall through which a cable of the arm (as described hereinafter) can extend. Means are preferably provided for holding the proximal portions of the arms in the receptacles and can include one or more of the doors, clamps, locks, friction fits, bolts, etc.

Regardless of what mechanism is used to mount the arms to the platform, the mechanical means of coupling must be sufficiently strong such that the arm mounts 50 do not move relative to the central portion 21, thereby providing a unitary body when the platform 20 is affixed to an operating room structure.

Figure 7:
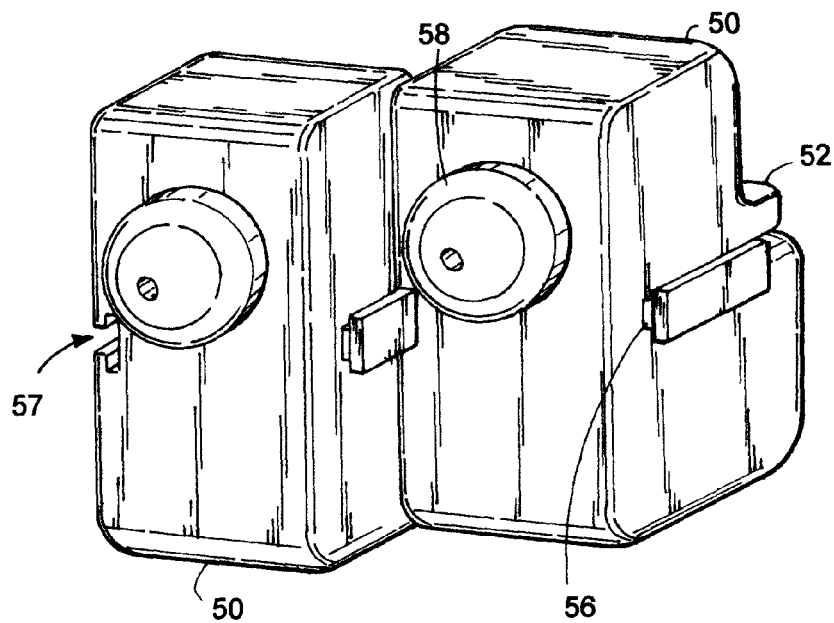
FIG. 7 is a front perspective view of the proximal portion of the arm module.
Figure 8:
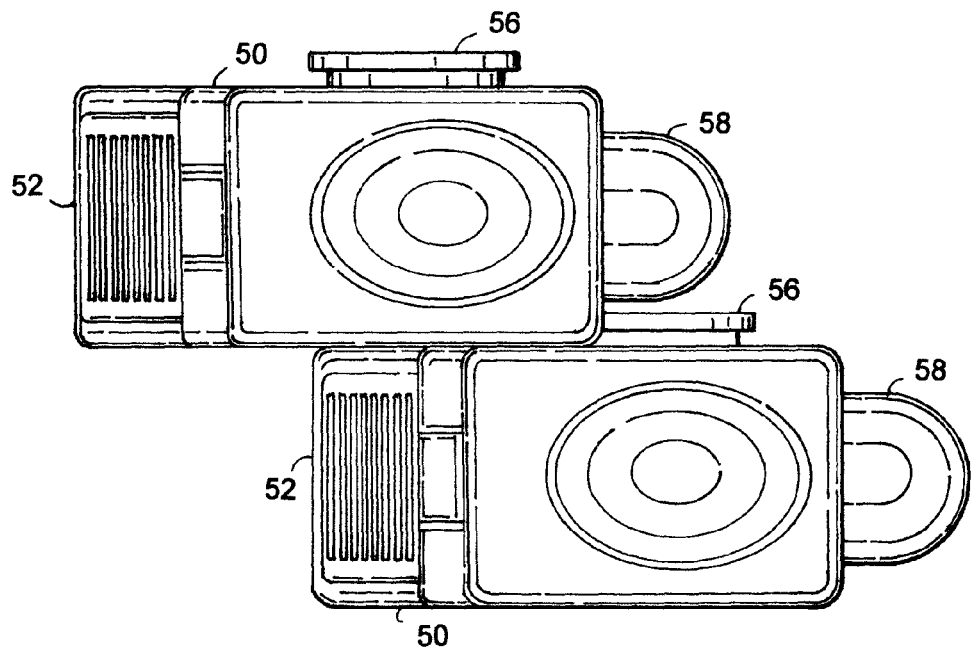
FIG. 8 is a top view of FIG. 7.
Figure 9:
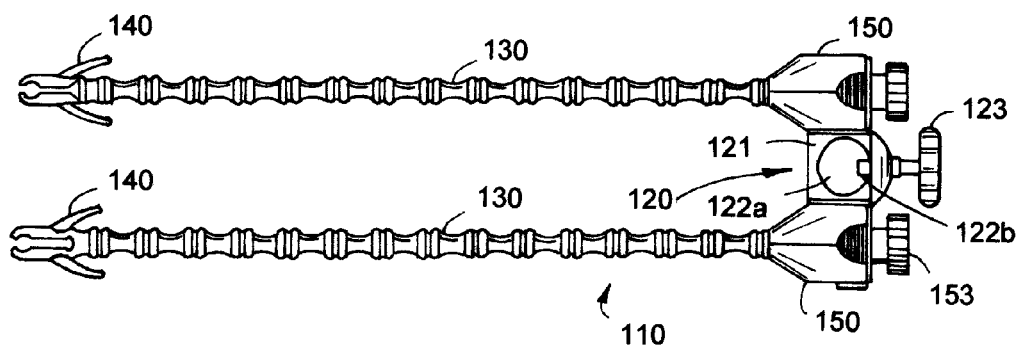
FIG. 9 is a top view of a medical assembly according to a second embodiment of the invention.

In the first embodiment of the invention, the arms 30 are modules having proximal ends which are coupled to the platform 20, flexible middle portions, and distal ends onto which the graspers 40 are fixed. More particularly, and as seen best in FIGS. 7 and 8, the proximal end of arms 30 comprises a modular mount 50 which can be affixed to the platform 20 and/or to one another using male-female coupling elements. In FIGS. 7 and 8 the arm mounts 50 are shown having rails 56 protruding outward from one side wall and grooves or slots 57 formed in the other side wall. The rails 56 are sized to mate snugly with the slots. In this manner, the platform 20 of the medical assembly 10 can be extended to include three or more arm mounts 50 for the placement of the arms 30 as needed by the physician depending on the number or arms 30 needed for a particular procedure. The arm mounts 50 may alternatively be connected by other forms of male-female connectors as envisioned by one of ordinary skill in the art. Although different numbers of arm mounts may be laterally attached to the platform 20, the medical assembly 10 preferably includes between two and six arm mounts 50.

Figure 5:
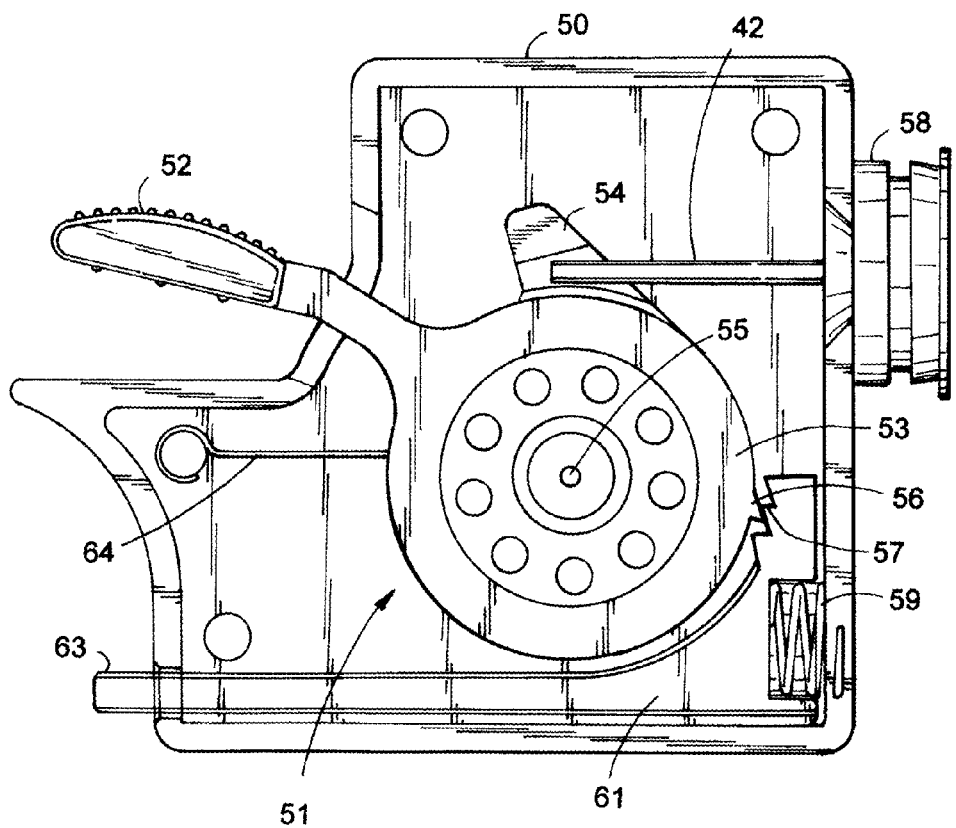
FIG. 5 is a mostly cross-sectional view of the proximal end of the arm module of FIG. 3.

The proximal portion of the arms internal to the arm mounts 50 is seen best with reference to FIG. 5 where the proximal end of each arm 20 is shown to include a cable tensioning and release winch-type mechanism 51. The cable tensioning and release winch mechanism 51 includes a winch 53 having a handle 52, a cable connector 54 which receives the proximal end of a cable 42 of the arm 30, an engagement/locking tooth 55, an axle 56, a braking rack 57, and a brake release 61. The brake release 61 is coupled to the mount 50 and spring loaded to a braking position by spring 59 which is coupled to the mount 50. The winch 51 is further stabilized in the mount 50 by stabilizer 64. As will be appreciated by those skilled in the art, when the handle 52 of the winch mechanism 51 is pulled (rotated) down, the winch wheel 53 rotates counterclockwise about axle 55 and the cable connector 54 pulls the cable 42 proximally. At the same time, locking tooth 56 moves past one or more teeth of the braking rack, and due to spring 59, the tooth and the braking rack prevent the winch wheel 53 from rotation. If it is desired to release the cable, an extension 63 of the rack is pushed counter to spring 59, thereby moving the rack 57 out of engagement with the locking tooth 56, and permitting rotation of the handle 52 in a clockwise direction.

Figure 3:
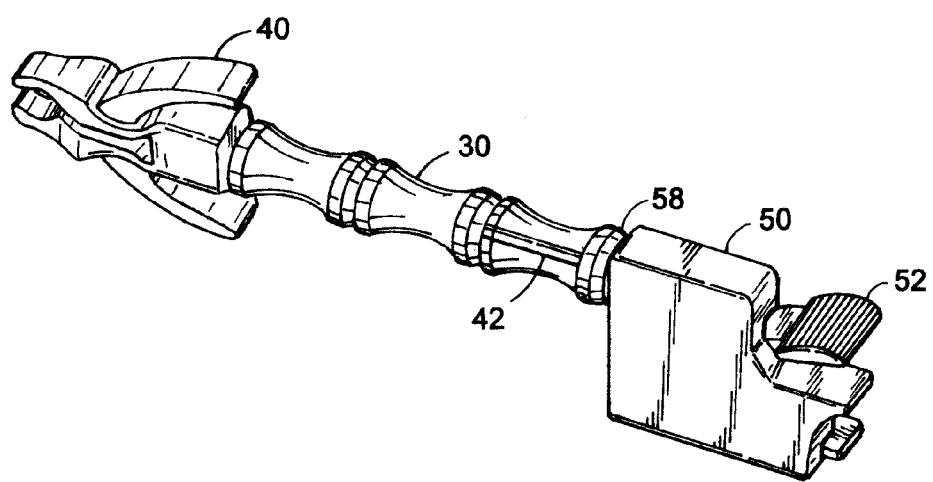
FIG. 3 is a perspective, partially transparent view of an arm module of FIG. 1.
Figure 4:
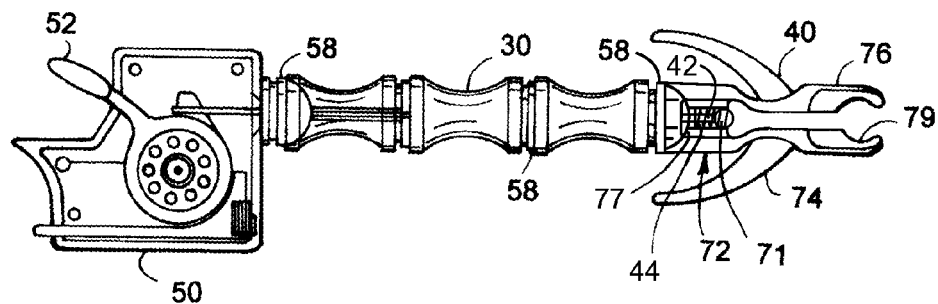
FIG. 4 is a partially transparent side view of the arm module of FIG. 3

As seen best in FIGS. 3 and 4, the flexible middle portion of arms 30 comprises a plurality of hollow arm segments or links 66 which are coupled by ball and socket joints 58 through which a tightening element such as the cable 42 extends. The joints allow the surgeon to directionally adjust the shape and position of each arm into a desired configuration (see e.g., FIG. 6), and are preferably roughened so that they maintain their configuration when set and fixed. The cable 42 is used to fix (tighten) the arm in its desired configuration. Thus, on its proximal end, the cable 42 extends through the mount 50 and is connected to the winch at winch connector 54.

Figure 6:
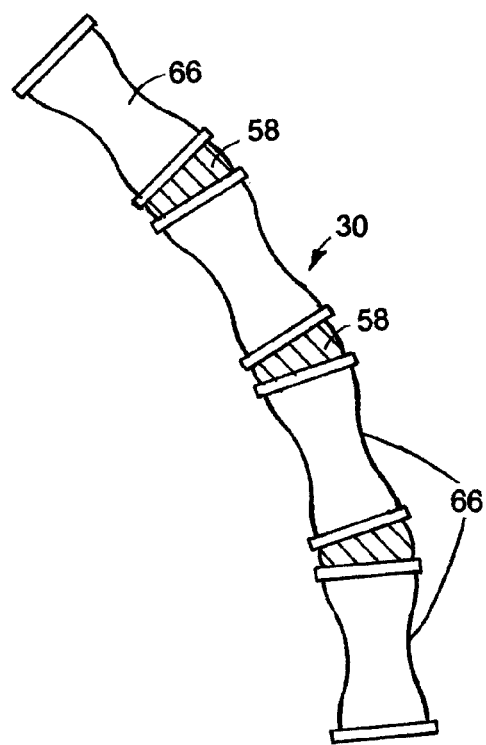
FIG. 6 is a perspective view of a plurality of arm segments of the arm module of FIG. 3 coupled by ball and socket joints.

More particularly, the arm segments or links 66 are preferably formed of a plastic material. The length of each arm may be controlled by the number of links 66 utilized. In addition, the configuration of each arm 30 can be changed via use of the ball and socket joints 58 which are preferably formed of a metal or other material which is harder than the links 66. Thus as seen in FIG. 6, the ball and socket joints 58 of the arm 30 allow rotational freedom of movement between each link 66 thereby creating multiple angled joints and permitting the arms 30 to assume a variety of geometrical configurations as needed by the surgeon during an operation. This rotational freedom of movement between the links 66 allow the arms 30 to be directionally adjustable into optimum positions desired by the operating physician. The physician may form a plurality of geometric configurations with the arms 30 such as e.g., arches, multi-pivoted extensions. The ball and socket joints 58 preferable have roughened surfaces so that strong frictional forces can maintain adjacent links 66 in positions fixed by the physician when tension is applied to the cable 42 via use of handle 52.

On its distal end, each arm 30 of the medical assembly 10 terminates at a grasper 40. More particularly, the grasper 40 is joined to a distal end of each arm 30 at a ball and socket joint 58 while the distal end of the cable 42 of the arm 30 terminates at a ball 71 which is captured by the grasper 40 as described in more detail hereinafter. Surrounding the cable just proximal of the ball is a spring 44 which is also captured by the grasper. By extending throughout the entire length of the arm 30, the cable 42 can provide compressive tension to the arm 30 which assists in the retention of the head 40 to the arm 30. As the links 34 of the arm 30 are rotated about adjoining ball and socket joints, the tension on the spring 44 increases due to the resulting increased tension of the cable 42.

Figure 2:
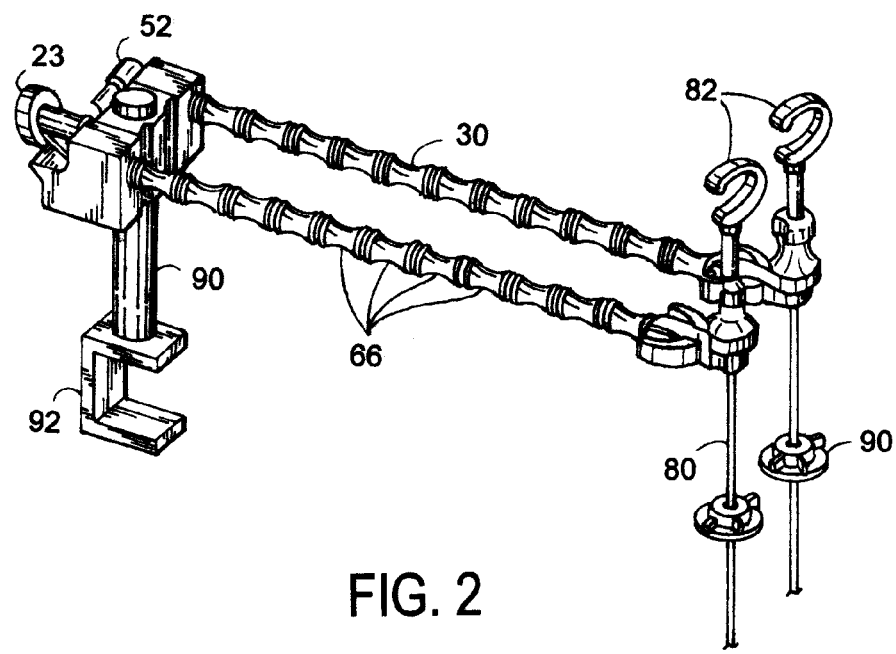
FIG. 2 is a perspective view of the medical assembly of FIG. 1 holding surgical instruments which are extending into surgical ports.

In the embodiment seen in FIGS. 1-4, the grasper 40 is formed as a one-piece, molded resilient plastic unit that is attached to the end of the arm 30 and will fit around and grasp a surgical instrument 80. More particularly, each grasper has a proximal connector portion 72 which is coupled to its associated arm 30, as well as handles 74, and distal grasping elements 76. The proximal connector 72 defines a concave receptor 77 which is adapted to receive a ball of a socket joint 58. It also defines a chamber 78 which is adapted to receive and trap the ball 71 at the end of the cable 42 and the spring 44 surrounding the cable 42. By receiving the socket joint 58 and by receiving and trapping the ball 71 of the cable 42, the distal grasper 40 is coupled to the arm 30. The handles 74 are coupled to the body of the grasper 40 distal of the proximal connector portion 72 and proximal of the grasping elements 76. The handles extend outward and backward (proximally) much like pliers handles. Because the handles 74 are integral with the grasping elements 76, when the handles are squeezed together the handles 74 cause the grasping elements 76 to open relative to each other, and when released, the handles 74 return to an at-rest position as the grasping elements 76 close. The grasping elements may take any of various forms but are preferably jaw-type elements each with an arced surface 79 which can grasp and securely hold a shaft of a laparoscopic instrument or port. Different graspers may be provided to receive different surgical instruments or ports; e.g., instruments or ports of different shaft diameters. Preferably, in an at-rest position, the arced surfaces 79 help define a circle of a diameter smaller than the diameter of the instrument or port which is to be held. Thus, as seen in FIG. 2, the graspers 40 of the assemblies 10 are grasping an outer needle port 80 through which surgical instruments extend.

A second embodiment of the invention is seen in FIGS. 9-16 where medical assembly 110 is shown having a platform 120 and arms 130 with graspers 140 located on the distal ends of the arms 130. The platform 120 preferably includes structure for affixing the platform in position relative to a patient on an operating room table, and structure for receiving the arms of the assembly. In a preferred embodiment, the platform 120 preferably includes a central portion 121 which acts as a nexus upon which other elements of the medical assembly 10 may be adjoined. Central portion 121 defines a first hole 122a and a second threaded hole 122b. The first hole 122a is designed to receive a support pole (note shown). The second hole 122b is designed to receive a threaded knob 123 or other mechanism for engaging the pole. More particularly, the hole 122a is optimally sized so that when the pole is inserted through the hole 122a, the platform 120 is slidably fixed along a longitudinal axis defined by the length of the pole. The knob 123 is then used to extend through hole 122b and fix the platform 120 relative to the pole. When the knob 123 is engaged, the platform 120 is fixed such that the platform cannot move in either the longitudinal direction along the length of the pole or in a rotational manner around the pole. In this manner, the platform positioning can be adjusted in a desired manner with the location of the platform relative to the patient being fixed.

The platform 120 also includes structure for receiving the arms 130 of the assembly. More particularly a platform structure for receiving the arms 130 comprises a rail and groove structure such that a housing or mount 150 on the proximal portion of the arms can slide into engagement with the platform. By providing platform 120 with one rail 156 and one groove 157, and the housing 150 of the proximal portion of the arms with one rail and one groove, a modular system is generated so that as many arms as necessary can be added to the system as suggested by FIG. 11.

Figure 10:
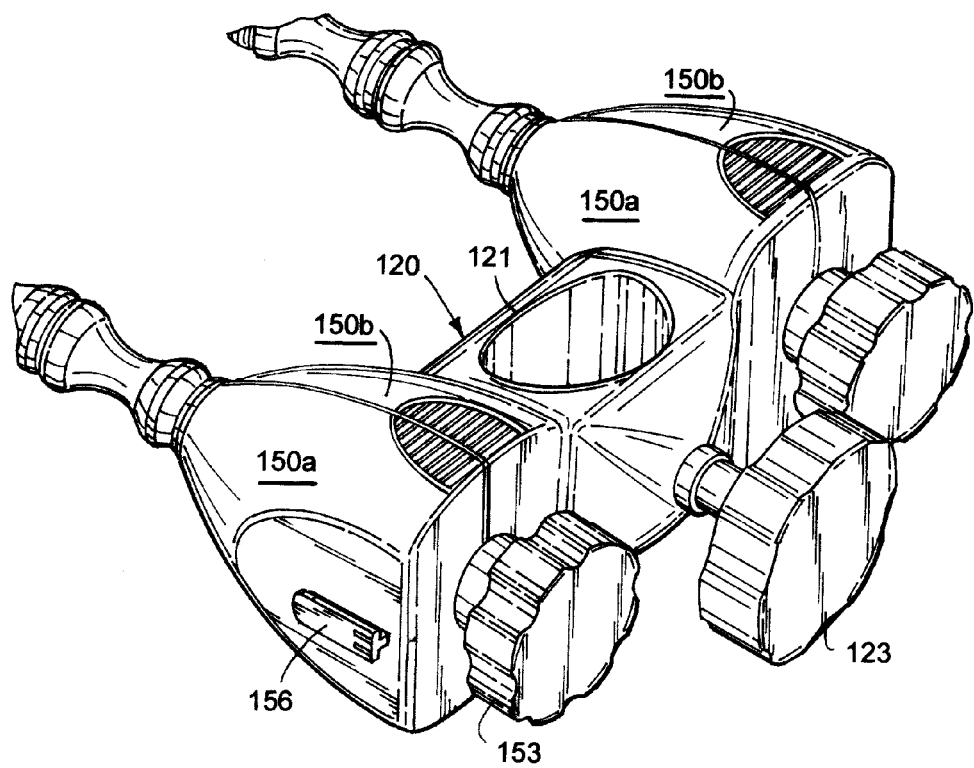
FIG. 10 is a perspective view of the proximal end of the assembly of FIG. 9.
Figure 11:
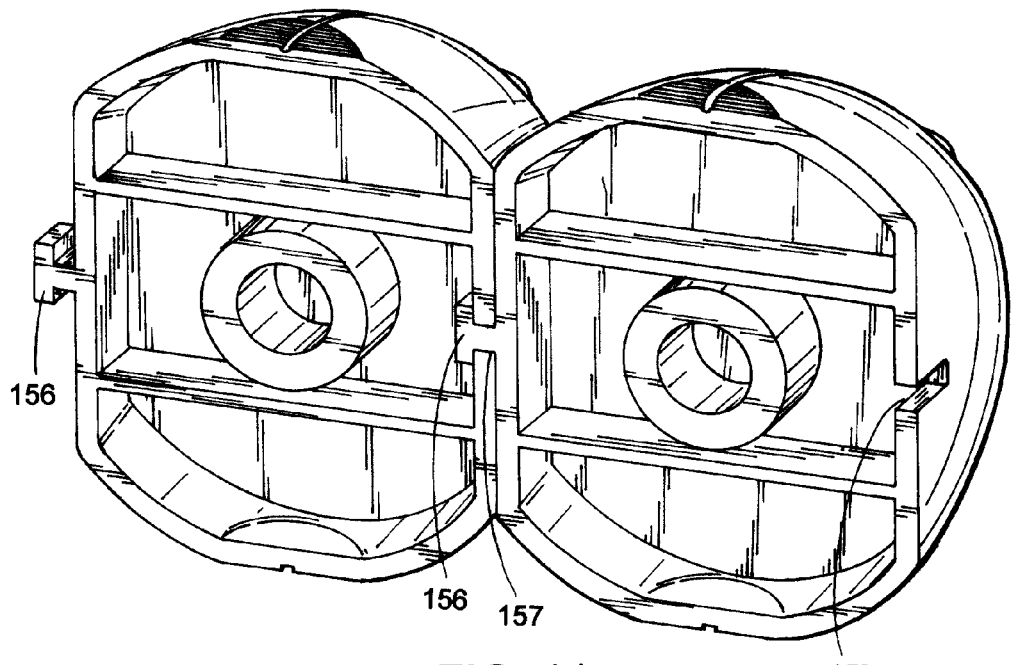
FIG. 11 is a rear cross-sectional view illustrating a rail and groove structure for coupling arm mounts of the second embodiment.

In the second embodiment of the invention, the arms 130 are modules having proximal ends which are coupled to the platform 120, flexible middle portions, and distal ends onto which the graspers 140 are fixed. More particularly, and as seen best in FIGS. 10 and 11, the proximal end of arms 130 comprises a modular mount 150 which can be affixed to the platform 120 and/or to one another using male-female coupling elements. In FIGS. 10 and 11 the arm mounts 150 are shown having rails 156 protruding outward from one side wall (mount portion 150a) and grooves or slots 157 formed in the other side wall (mount portion 150b). The rails 156 are sized to mate snugly with the slots. In this manner, the platform 120 of the medical assembly 110 can be extended to include three or more arm mounts 150 for the placement of the arms 130 as needed by the physician depending on the number of arms 130 needed for a particular procedure. The arm mounts 150 may alternatively be connected by other forms of male-female connectors as envisioned by one of ordinary skill in the art. Although different numbers of arm mounts may be laterally attached to the platform 120, the medical assembly 110 preferably includes between two and six arm mounts 150.

Figure 12:
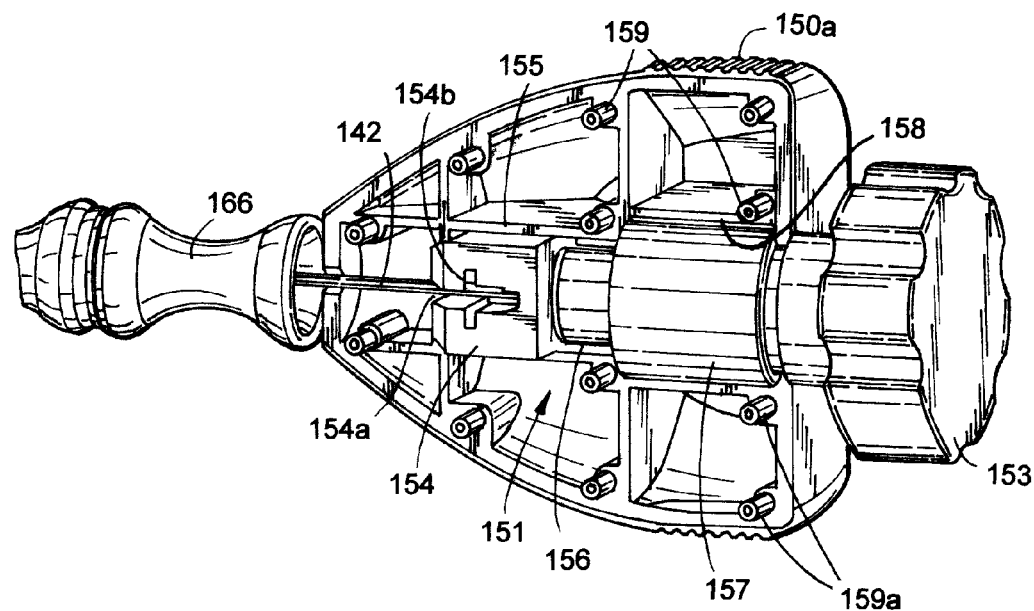
FIG. 12 is a partial cross-sectional partial perspective view of the proximal arm portion of FIG. 9.
Figure 13:
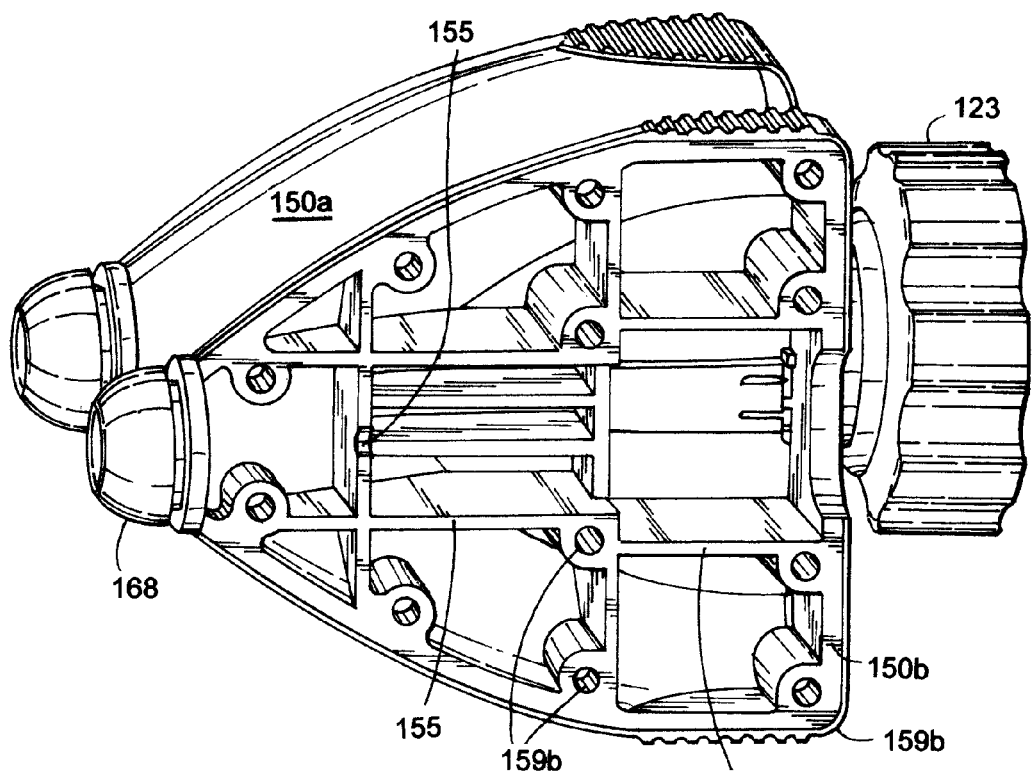
FIG. 13 is a partial cross-section partial perspective view of a mating proximal arm portion for FIG. 12.

The proximal portion of the arms internal to the arm mounts 150 is seen best with reference to FIGS. 12 and 13 where the proximal end of each arm 120 is shown to include a cable tensioning and release mechanism 151. More particularly, as seen in FIG. 12, the proximal end of the cable 142 is captured by a block 154 which includes a longitudinal slot 154a for the cable and a vertical slot 154b for capturing a disk (not shown) which is fixed to the cable 142. The block 154 cannot rotate because it is captured in compartment 155. However, the block 154 is coupled to a first cylinder 156 which has a proximal end having external threads (not shown). The first cylinder 156 mates with a second cylinder 157 having internal threads (not shown). The second cylinder 157 is coupled to knob 153 which extends through the rear wall of the arm mount 150. The second cylinder 157 cannot move axially because it is trapped in a compartment 158. Rotation of knob 153 causes rotation of the second cylinder 157 which causes linear translation of the first cylinder 156 and the block 154, thereby causing the cable 142 to translate linearly.

The compartments 155 and 158 in which block 154 and second cylinder 157 are respectively captured are formed by the coupling of mount portions 150a and 150b. Thus, as seen in FIG. 12, mount portion 150a includes a plurality of lugs 159a (twelve shown) while as seen in FIG. 13, mount portion 150b includes a plurality of lug receivers 159b (twelve shown). Also, as seen in FIG. 13, coupled to the front of the mount 150 is a ball-type joint 168.

As previously indicated, the flexible middle portion of arms 130 a plurality of hollow arm segments or links 166 which are coupled by joints 168 through which a tightening element such as cable 142 extends. The length of each arm may be controlled by the number of links 166 utilized. The joints 168 allow the surgeon to directionally adjust the shape and position of each arm into a desired configuration. More particularly, the joints 168 of the arm 130 allow rotational freedom of movement between each link 166 thereby creating multiple angled joints and permitting the arms 130 to assume a variety of geometrical configurations as needed by the surgeon during an operation. The cable 142 is used to fix (tighten) the arm in its desired configuration.

Figure 14:
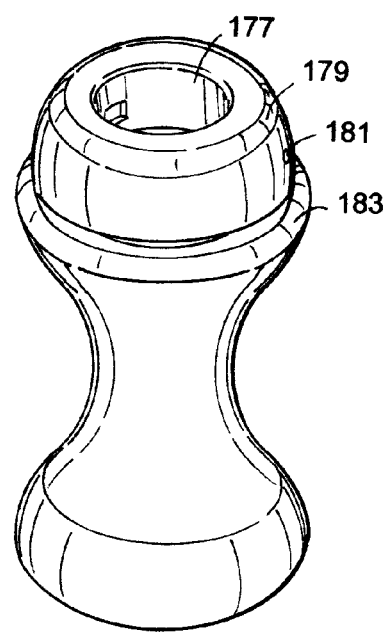
FIG. 14 is a perspective view of an arm segment of the assembly of FIG. 9.
Figure 15:
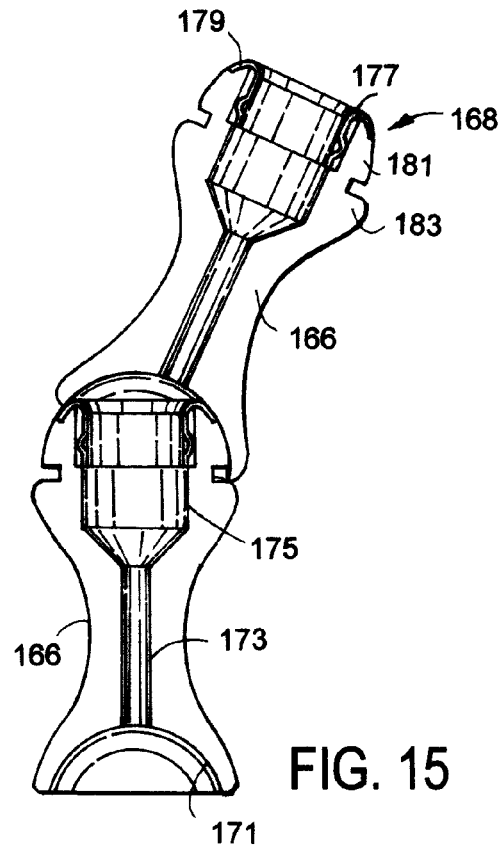
FIG. 15 is a cross-sectional view of two mated arm segments of the assembly of FIG. 9.

As seen in FIGS. 14 and 15, each link 166 defines a partial-spherical concavity 171 or socket on one end, a hollow passageway 173, and a stepped distal chamber 175 through which the cable 142 (FIGS. 12 and 16) can extend. The outer configuration of the links 166 are shown are generally hourglass in shape. However, other shapes could be utilized. The chamber 175 receives a clip 177 which presents a rounded outer surface 179, and which is affixed in the chamber 175. The rounded outer surface 179 continues a surface 181 of the distal portion of the link 166 so that together, surfaces 179 and 181 function as a ball-type joint 168. Preferably, the clip 177 is formed from a metal, alloy, or hardened polymer-based material, and the rounded outer surface 179 of the clip 177 is roughened. Preferably, the link 166 is made from a plastic or softer material than the clip 177. With the provided arrangement, the ball-type joint 168 of one link 166 is received in the socket 171 of a next link (as shown in FIG. 15), and rotational freedom of movement is permitted. The extent of rotational freedom is limited by a stop in the form of a ledge 183 on the link. Because the clip 177 is roughened, when one link is manipulated relative to another, the clip of a link tends to dig into the concavity surface of the adjacent link 166 and take a fix.

Returning to FIG. 13, it will be appreciated that the ball-type joint 168 provided on the distal end of the mount 150 is preferably substantially identical to the joint 168 shown and described in FIGS. 14 and 15.

Figure 16:
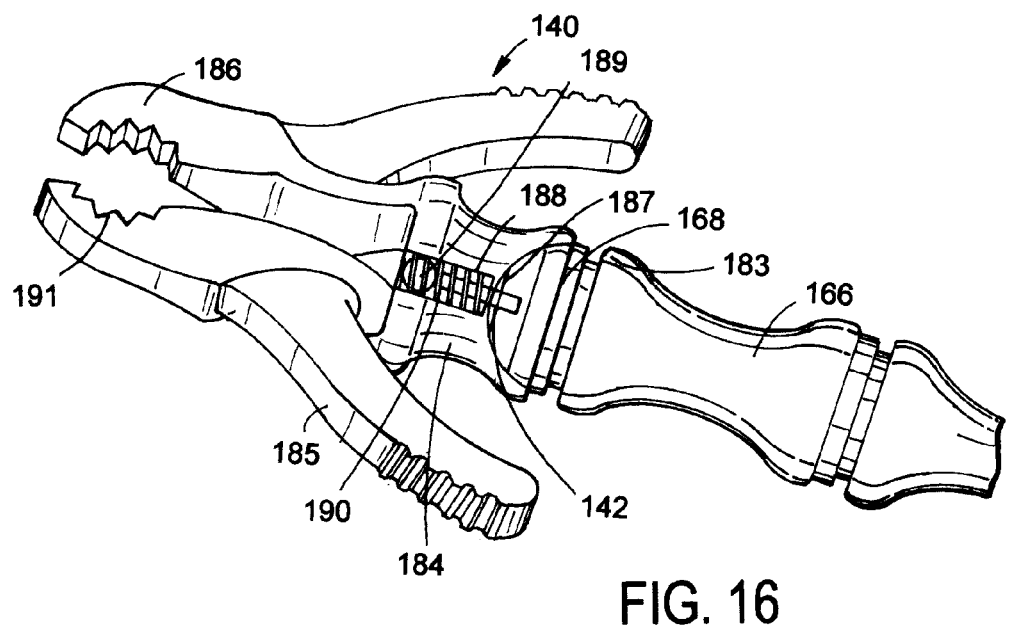
FIG. 16 is a partially transparent view of the distal end of the assembly of FIG. 9.

Turning now to FIG. 16, the grasper 140 is formed as a one-piece, molded resilient plastic unit that is attached to the end of the arm 130 and will fit around and grasp a surgical instrument. More particularly, each grasper has a proximal connector portion 184 which is coupled to its associated arm 130, as well as handles 185, and distal grasping elements 186. The proximal connector 184 defines a concave receptor or socket 187 which is adapted to receive a ball of a socket joint 168. It also defines a chamber 188 which is adapted to receive and trap the ball 189 at the end of the cable 142 and the spring 190 surrounding the cable 142. By receiving the socket joint 168 and by receiving and trapping the ball 189 of the cable 142, the distal grasper 140 is coupled to the arm 130. The handles 185 are coupled to the body of the grasper 140 distal of the proximal connector portion 184 and proximal of the grasping elements 186. The handles extend outward and backward (proximally) much like pliers handles. Because the handles 185 are integral with the grasping elements 186, when the handles are squeezed together the handles 185 cause the grasping elements 186 to open relative to each other, and when released, the handles 185 return to an at-rest position as the grasping elements 186 close. The grasping elements may take any of various forms but are preferably jaw-type elements each with a serrated arced surface 191 which can grasp and securely hold a shaft of a laparoscopic instrument or port. Different graspers may be provided to receive different surgical instruments or ports; e.g., instruments or ports of different shaft diameters.

In use, prior or during surgery, it is desirable to locate assembly 110 on a surgical fixture such as a operating room table pole by sliding platform 120 over the pole and fixing the location of the platform 120 relative to the pole using knob 123. Prior to fixing platform 120 relative to the pole, or thereafter, one or more arms 130 are attached to the platform 120 using the rail and slot mechanisms 156, 157. If more arms 130 are required for the surgery, prior to fixing the platform 120 relative to the pole, or at any time, arms 130 may be attached to other arms using the rail and slot mechanisms. When it is desired to fix the location of a medical instrument relative to a patient, an arm 130 having a distal grasper 140 is manipulated by the surgeon to a desired position, and the graspers 140 are manipulated to cause the grasper to grasp the medical instrument or port through which the medical instrument extends. Prior to manipulating the grasper or thereafter, the arm 130 is fixed in place by tightening knob 153 and thereby providing tension on cable 142. The tension on the cable, in turn, causes the links 166 to fix relative to each other with the ball-type joints 168 in the partial spherical concavities 171 of adjacent links. This procedure can be utilized with respect to as many instruments and arms 130 that are utilized. If it is desired to change the position of any grasper 140, the tension of the associated cable can be released by rotating the associated knob in an opposite direction, moving the associated arm 130 and grasper 140 to a desired position, and then retightening the associated knob 153 to fix the arm 130 in place.

There have been described and illustrated herein several embodiments of a medical assembly and methods for the use thereof. While particular embodiments of the invention have been described, it is not intended that the invention be limited thereto, as it is intended that the invention be as broad in scope as the art will allow and that the specification be read likewise. Thus, while particular arrangements have been shown and described for coupling a platform to an operating room fixture, it will be appreciated by those skilled in the art that other arrangements could be utilized. Likewise, while particular arrangements have been shown and described for coupling arms to the platform and/or to each other, it will be appreciated by those skilled in the art that other mechanisms could be utilized including but not limited to snaps and snap receivers, screws or bolts, loops and hooks, etc. Further, while particular mechanisms have been described which provide flexible arms which can be manipulated into a desired form (e.g., a tortuous path or otherwise), it will be appreciated that other mechanisms can be utilized. Thus, for example, a pliable coil such as used for certain lamps could be utilized in lieu of the ball and socket link arrangement described. Also, while arms of the same length are shown for two different embodiments, it will be appreciated that arms of different lengths could be utilized. Further yet, while a one-piece grasper was described for grasping a shaft of a medical instrument or port, it will be appreciated that the grasper could be made from multiple pieces and could assume various arrangements. It will therefore be appreciated by those skilled in the art that yet other modifications could be made to the provided invention without deviating from its spirit and scope as claimed.

What is claimed is:

1. A medical assembly for use in conjunction with a fixture, the medical assembly for holding medical devices extending into a patient in a fixed position relative to the patient, comprising:
   a) a platform having coupling means for coupling to the fixture, said platform supported by said fixture; and
   b) a plurality of flexible arms removably coupled to said platform and extending therefrom, said arms each capable of being fixed in a tortuous path and each having a proximal arm mount and a distal grasping means for grasping the respective medical devices;
   wherein said platform includes a first side disposed opposite a second side, said first side including first attachment means for removable direct coupling to an arm mount of one of said plurality of arms, said second side including second attachment means for removable direct coupling to an arm mount of another of said plurality of arms, and the arm mount of each one of said plurality of arms defining a third side opposite a fourth side, said third and fourth sides including third and fourth attachment means, respectively, that are adapted for removable direct coupling to said first and second attachment means of said platform as well as for removable direct coupling to an arm mount of another arm of the assembly.

2. The medical assembly according to claim 1, wherein: each arm comprises a plurality of links.

3. The medical assembly according to claim 2, wherein: each of said plurality of links includes a socket, and each arm comprises a plurality of ball-type joints which engage a respective link socket.

4. The medical assembly according to claim 1, wherein: each arm includes a tension cable.

5. The medical assembly according to claim 4, wherein: each arm includes means for tightening and loosening said cable.

6. The medical assembly according to claim 4, wherein:
said means for tightening and loosening comprises a winch mechanism which is coupled to a proximal end of said cable and which rotates to cause translational movement of said cable.

7. The medical assembly according to claim 4, wherein:
said means for tightening and loosening comprises a knob and threaded means coupled to said knob and to said cable, said threaded means for translating rotation of said knob into translational movement of said cable.

8. The medical assembly according to claim 1, wherein:
each said grasping means includes handles, opposed grasping elements coupled to said handles, and a proximal connector which is coupled to a respective arm.

9. A medical assembly according to claim 8, wherein:
each said grasping means is a one piece molded unit.

10. The medical assembly according to claim 8, wherein:
each said arm includes a cable, and
said proximal connector defines a socket which receives said arm and a chamber which captures a distal end of said cable.

11. The medical assembly according to claim 10, further comprising:
a spring around said distal end of said cable and captured in said chamber.

12. The medical assembly according to claim 1, wherein:
said first attachment means comprises a first rail;
said second attachment means comprises a first slot;
said third attachment means comprises a second rail; and
said fourth attachment means comprises a second slot;
wherein said second rail is adapted to be slidably received within said first slot for removable direct coupling of a respective arm mount to said platform or slidably received within a second slot of another respective arm mount for removable direct coupling of a pair of arm mounts; and
wherein said second slot is adapted to slidably receive said first rail for removable direct coupling of a respective arm mount to said platform or slidably receive a second rail of another arm mount for removable direct coupling of a pair of arm mounts.

13. The medical assembly according to claim 1, wherein:
said coupling means of said platform provides for relative movement of said platform relative to said fixture.

14. The medical assembly according to claim 1, wherein:
said coupling means of said platform comprises a pole; and
said platform defines a central hole for receiving said pole.

15. The medical assembly according to claim 14, wherein:
said coupling means of said platform further comprises a knob extending through a second hole in said platform orthogonal to said central hole, said knob for fixing said platform relative to said pole.

16. A method for holding a plurality of medical devices extending into a patient in fixed positions relative to a patient, said method comprising:
a) providing an assembly including a platform and a plurality of flexible arms, the platform having coupling means for coupling to a fixture that supports the platform, the plurality of flexible arms capable of being removably coupled to the platform and extending therefrom, said arms each capable of being fixed in a tortuous path and each having a proximal arm mount and a distal grasping means for grasping the respective medical devices, wherein the platform includes a first side disposed opposite a second side, said first side including first attachment means for removable direct coupling to an arm mount of one of said plurality of arms, said second side including second attachment means for removable direct coupling to an arm mount of another of said plurality of arms, and the arm mount of each one of said plurality of arms defining a third side opposite a fourth side, said third and fourth sides including third and fourth attachment means, respectively, that are adapted for removable direct coupling to said first and second attachment means of said platform as well as for removable direct coupling to an arm mount of another arm of the assembly;
b) coupling the platform to a fixture such that the platform is supported by the fixture;
c) removably coupling a respective arm mount for one of the plurality of arms directly to the platform using the first attachment means of the platform and one of the third and fourth attachment means of the respective arm mount;
d) removably coupling a respective arm mount for another of the plurality of arms directly to the platform using the second attachment means of the platform and one of the third and fourth attachment means of the respective arm mount;
e) manipulating the arms whose arm mounts where removably coupled to the platform in c) and d) into desired positions; and
f) manipulating the graspers of the arms whose arm mounts where removably coupled to the platform in c) and d) in order to grasp the respective medical devices.

17. The method according to claim 16, further comprising:
h) removably coupling at least one arm mount for an additional arm directly to at least one of the arm mounts removably coupled to the platform in c) and d) using one of the third and fourth attachment means of the at least one arm mount of the additional arm.

18. The method according to claim 17, wherein:
the arm mounts are held in positions offset laterally from the platform.

19. The method according to claim 16, further comprising:
g) removably coupling a respective arm mount for an additional arm directly to one of the arm mounts removably coupled to the platform in c) using one of the third and fourth attachment means of the respective arm mount.

20. The method according to claim 16, further comprising:
after said manipulating of e), applying tension to the arms whose arm mounts where removably coupled directly to the platform in c) and d) in order to fix such arms in the desired positions.

21. The method according to claim 16, wherein:
the fixture comprises a table or bed.

22. The method according to claim 16, wherein:
the coupling means of the platform provides for relative movement of the platform relative to the fixture; and
the method further includes using the coupling means to adjust position of the platform relative to the patient.

* * * * *